(12) United States Patent
Mukundan et al.

(10) Patent No.: US 6,605,202 B1
(45) Date of Patent: Aug. 12, 2003

(54) ELECTRODES FOR SOLID STATE GAS SENSOR

(75) Inventors: Rangachary Mukundan, Santa Fe, NM (US); Eric L. Brosha, Los Alamos, NM (US); Fernando Garzon, Santa Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 10/175,252

(22) Filed: Jun. 18, 2002

Related U.S. Application Data

(63) Continuation of application No. 09/770,359, filed on Jan. 25, 2001, now abandoned.

(51) Int. Cl.$^7$ ............................................. G01N 27/407
(52) U.S. Cl. ...................... 204/424; 204/421; 205/781; 205/784.5; 205/787; 264/109; 264/239; 264/271.1; 264/272.11; 264/272.12; 264/272.15; 264/614; 264/618; 264/681
(58) Field of Search ................................. 204/421–429

(56) References Cited

U.S. PATENT DOCUMENTS

| | | | |
|---|---|---|---|
| 3,216,911 A | 11/1965 | Kronenberg et al. ........... 204/1 |
| 3,576,730 A | 4/1971 | Spacil ........................ 204/195 |
| 3,723,589 A | 3/1973 | Kennedy ..................... 264/101 |
| 4,096,048 A | * 6/1978 | Matsumoto et al. |
| 4,177,125 A | 12/1979 | Barnabe ...................... 204/195 |
| 4,220,517 A | 9/1980 | Niwa et al. .................. 204/195 |
| 4,277,323 A | 7/1981 | Muller et al. ................ 204/195 |
| 4,304,651 A | 12/1981 | Wakizaka et al. ............ 204/195 |
| 4,395,319 A | * 7/1983 | Torisu et al. |
| 4,462,891 A | 7/1984 | Lawless ....................... 204/427 |
| 4,786,374 A | 11/1988 | Worrell et al. ................. 204/1 |
| 5,173,166 A | 12/1992 | Tomantschger et al. .... 204/412 |
| 5,958,214 A | 9/1999 | Nikolskaja ................... 205/784 |

OTHER PUBLICATIONS

Mukundan et al., "Ceria–Electrolyte–Based Mixed Potential Sensors for the Detection of Hydrocarbons and Carbon Monoxide," Electrochemical and Solid–State Letters, 2 (8) 412–414 (1999) Month unavailable.

Miura et al., "Mixed–Potential–Type Propylene Sensor Based on Stabilized Zirconia and Oxide Electrode," Electrochemistry Communications, 2 (2000) Month unavailable 77–80.

(List continued on next page.)

Primary Examiner—T. Tung
(74) Attorney, Agent, or Firm—Ray G. Wilson

(57) ABSTRACT

A mixed potential electrochemical sensor for the detection of gases has a ceria-based electrolyte with a surface for exposing to the gases to be detected, and with a reference wire electrode and a sensing wire electrode extending through the surface and fixed within the electrolyte as the electrolyte is compressed and sintered. The electrochemical sensor is formed by placing a wire reference electrode and a wire sensing electrode in a die, where each electrode has a first compressed planar section and a second section depending from the first section with the second section of each electrode extending axially within the die. The die is filled with an oxide-electrolyte powder and the powder is pressed within the die with the wire electrodes. The wire-electrodes and the pressed oxide-electrolyte powder are sintered to form a ceramic electrolyte base with a reference wire electrode and a sensing wire electrode depending therefrom.

6 Claims, 2 Drawing Sheets

OTHER PUBLICATIONS

Hibion, et al., "High–Temperature Hydrocarbon Sensors Based on a Stabilized Zirconia Electrolyte and Metal Oxide Electrodes," Electrochemical and Solid–State Letters, 2 912) 651–653 (1999) Month unavailable.

Miura et al., "Mixed Potential Type $NO_2$ Senosr Based on Stabilized Zirconia and Oxide Electrode," Electrochem. Soc., vol. 143, No. 2, pp. 33–35, Feb. 1996.

Li et al., "High–temperature Carbon Monoxide Potentiometric Sensor," J. Electrochem. Soc., vol. 140, No. 4, pp. 1068–1073, Apr. 1993.

Miura et al., "Highly Slective CO Sensor Using Stabilized Zirconia and a Couple of Oxide Electrodes," Sensors and Actuators B 47, (1988) Month unavailable 84–91.

Williams et al., "Solid Electrolyte Mixed Potential Phenomena," Solid State Chemistry 1982, Proceedings of the Second European Conference, Veldhoven, The Netherlands, Jun. 7–9, 1982, R. Metselaar, H.J.M. Heijlgers and J. Schoonman (Eds), Studies in Inorganic Chemistry, vol. 3.

* cited by examiner

ELECTRODES FOR SOLID STATE GAS SENSOR

RELATED APPLICATIONS

This application is a continuation of U.S. patent application Ser. No. 9/770,359, filed Jan. 25, 2001 now abandoned.

STATEMENT REGARDING FEDERAL RIGHTS

This invention was made with government support under Contract No. W7405-ENG-36 awarded by the U.S. Department of Energy. The government has certain rights in the invention.

FIELD OF THE INVENTION

The present invention relates generally to solid state gas sensors, and, more particularly, to mixed-potential sensors based on oxygen-ion conducting electrolytes.

BACKGROUND OF THE INVENTION

Mixed potential gas sensors are currently being developed for combustion control and environmental monitoring applications. The devices typically are comprised of two different catalytic electrodes deposited on a solid electrolyte. Multiple reduction-oxidation reactions occurring between the gas-phase and the electrodes cause mixed potentials of differing magnitude to develop at the dissimilar electrodes. The differences in heterogeneous kinetics, electrokinetics and the equilibrium potentials for these reactions all influence the device response to varying concentrations of analyte gas.

An example of a mixed potential device is a carbon monoxide sensor consisting of a porous platinum electrode and a porous gold electrode deposited on a zirconia based oxide electrolyte. The following electrochemical reactions occur on both the gold and platinum triple phase interfaces at differing rates:

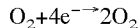
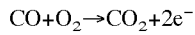

$O_2 + 4e^- \rightarrow 2O^{2-}$ $CO + O^{2-} \rightarrow CO_2 + 2e^-$

Mixed-potential sensors based on oxygen-ion conducting electrolytes have been studied since D. E. Willams et. al. demonstrated the working of a "Pt/YSZ/Au" CO-sensor operating at $T \leq 400°$ C. Since that time several metal and metal-oxide electrodes have been used to design various mixed-potential sensors for the detection of CO, $NO_x$ and hydrocarbons. Although all these sensors do give a response in the presence of reducing-gases, their lack of stability, reproducibility and selectivity have hindered the commercial development of sensors based on this technology.

Various objects, advantages and novel features of the invention will be set forth in part in the description which follows, and, in part, will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention includes a mixed potential electrochemical sensor for the detection of gases. A ceria-based electrolyte is formed with a surface for exposing to the gases to be detected, and with a reference wire electrode and a sensing wire electrode extending through the surface of the electrolyte and fixed within the electrolyte as the electrolyte is compressed and sintered.

The electrochemical sensor is formed by placing a wire reference electrode and a wire sensing electrode in a die, where each electrode has a first compressed planar section and a second section depending from the first section with the second section of each electrode extending axially within the die. The die is filled with an oxide-electrolyte powder and the the powder is pressed within the die with the wire electrodes. The wire-electrodes and the pressed oxide-electrolyte powder are sintered to form a ceramic electrolyte base with a reference wire electrode and a sensing wire electrode depending therefrom.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION

This invention is a mixed-potential electrochemical sensor for the detection of gases, such as CO, NO, and non-methane hydrocarbons, in room air. The sensor utilizes a ceria-based electrolyte, and metal wire electrodes. The stability and reproducibility of the sensor is achieved by using wire electrodes instead of the usual thin or thick film electrodes that are currently employed. The metal wire-electrodes are directly embedded into the electrolyte and co-sintered in order to produce a stable metal/electrolyte interface. A suitable ceria-based electrolyte is $Ce_{1-x}A_xO_{2-x/2}$, where $0 \leq x \leq 0.25$ and A is selected from Y, Sc, or Lanthanide.

The selectivity of the device is achieved by the proper selection of the metal wire-electrodes used. Pt is used as a pseudo-reference electrode and the sensing electrode can be selected form a wide variety of metals or alloys, based on the gas that is to be sensed. For example, a Au wire is used to sense CO in room air; other precious metal wires such as Ag, Pd, or Rh can be used, depending on the gas to be detected.

The specific approach involves the following steps:

1) Embedding the metal wires in the oxide-electrolyte powder.

2) Pressing the powder along with the embedded wires in a die to form the sensor.

3) Polishing off the excess electrolyte powder in order to expose the metal wire-electrode.

4) Co-sintering the wire-electrodes along with the electrolyte powder in order to give mechanical strength and sufficient ionic-conductivity to the electrolyte.

Figure 1:
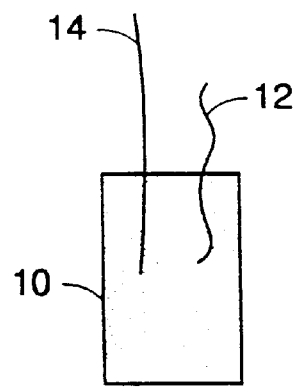
FIG. 1 is a cross-sectional view of a sensor according to one embodiment of the present invention.

FIG. 1 illustrates one embodiment of a sensor according to the present invention. Electrolyte body 10 is formed of $Ce_{0.8}Gd_{0.2}O_{1.9}$. Reference electrode 12 is formed of Pt and sensing electrode 14 is formed of Au. A $Ce_{0.8}Gd_{0.2}O_{1.9}$ powder (0.01–10 $\mu$m in diameter, and, preferably, 1–3 $\mu$m (Praixair)) was the starting material. The Au and Pt wires (Johnson Matthey) were 0.01" diameter. Suitable wires are 0.004" to 0.01" in diameter, with the lower size based on mechanical strength and the upper size limited by cost considerations.

Figure 2A:
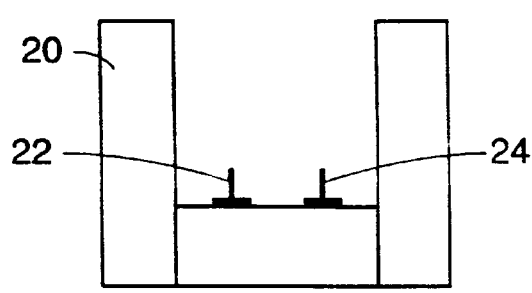
FIGS. 2A and 2B are side and top views showing a exemplary die for forming the sensor shown in FIG. 1.
Figure 2B:
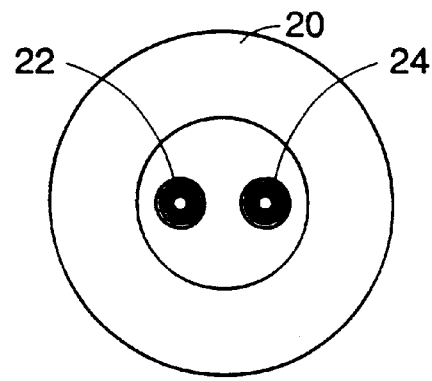

FIG. 2 illustrates aspects of the process used to produce the sensor shown in FIG. 1. Sensing electrode wire 22 and reference electrode wire 24 were first formed to have a first compressed planar section and a second section depending from the planar section and extending axially within die 20. The compressed planar section is formed from a length of wire that is coiled, looped, or otherwise twisted into a small planar area. As illustrated in FIG. 2, a coil is a simple embodiment to use.

The coiled electrode wires 22, 24 are placed on the base of die 20 (e.g., 1/4"–3/4" diameter) as illustrated in FIG. 2. The electrolyte powder (2–5 gms) was then poured on top of electrodes 22, 24 and was pressed at 3000–7000 psi for 5 minutes. In one embodiment, the pressure was created by a uni-axial press. Other suitable pressing processes are iso-static pressure (hot or cold) and extrusion. The resulting pellet was sintered in air at 1000–1050° C. for 10–16 hours. This resulted in an electrolyte that was ~70% of theoretical density. The low sintering temperature was chosen so as not to melt the Au-wire (melting point=1064.6° C.).

Figure 3:
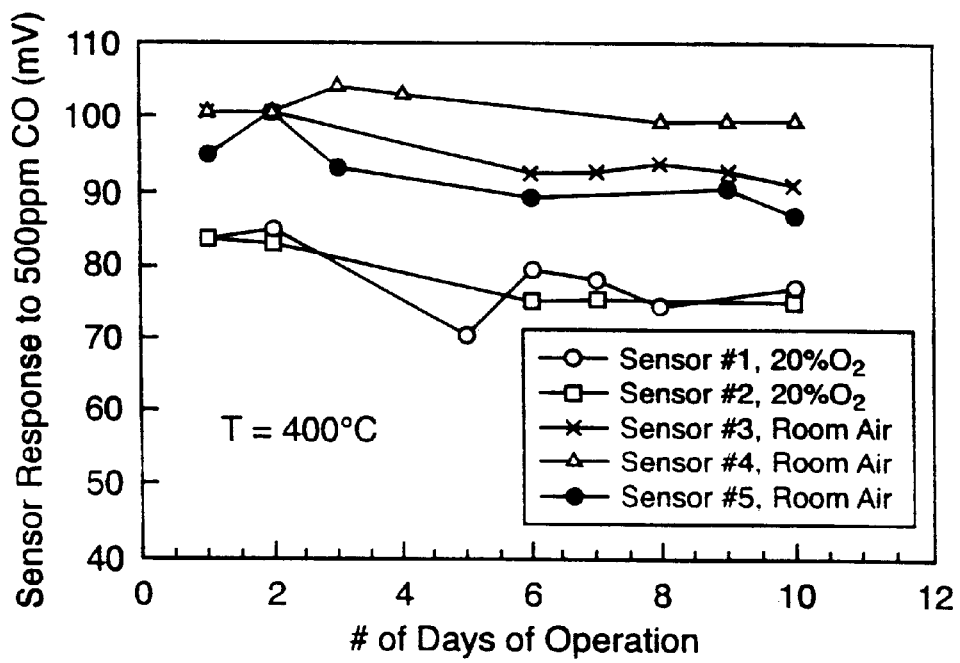
FIG. 3 graphically demonstrates the response to various gas mixtures of a variety of sensors formed in accordance with the present invention.

Five different sensors were prepared using the above method. Sensors #1–#3 were pressed in a 3/4" die, sensor #4 in a 1/2" die and sensor #5 in a 1/4" die. All sensors were then heated in a furnace and the sensor response was tested at 400° C. The response of all these sensors to 500 ppm CO in 20–21% $O_2$ up to 10 days of operation is presented in FIG. 3 It is seen that the three sensors tested in room air (Sensors #3–#5) had a relatively stable response of 95±8 mV to 500 ppm CO and a response of 40±4 mV for 100 ppm CO (not shown in figure). The other two sensors showed a lower response (80±5 mV) to 500 ppm CO because they were tested in a 20% $O_2$ base gas. These results indicate that the present invention results in stable and reproducible sensors.

Figure 4:
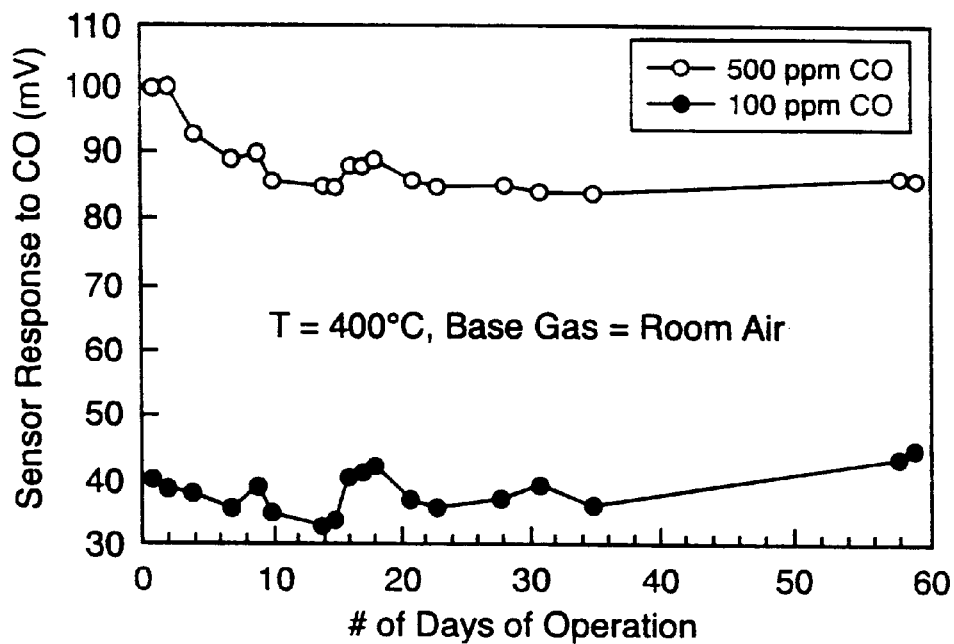
FIG. 4 graphically illustrates the stability of sensor #5 shown in FIG. 3.

Long term stability tests were performed on sensor #5 and the results are shown in FIG. 4. At 500 ppm CO the sensor response initially decayed from 100 mV to ~85 mV over a period of 10 days and after that was very stable for up to 60 days. At 100 ppm CO the sensor response was stable from the beginning and was 40±4 mV. This fluctuation of 10% in the signal from the CO was in part due to errors in the mass flow controllers. The controllers used in this experiment were manually adjusted and could control flows only to an accuracy of 5% at the 100 ppm level.

The major improvement over existing technology is that the sensor responses and sensor baseline are stable over time. Moreover the sensor response is easily reproducible from sensor to sensor and the variation is <10% of signal level. The sensor preparation consists only of standard solid-state synthesis and is very cheap. The electrodes and electrolytes are co-sintered and hence there is only one heat treatment step involved in the entire sensor preparation.

The second improvement over existing technology is that the "burn in" period before a stable signal is achieved is much shorter than existing semiconductor sensor technology. Semiconductor sensor devices must be preheated for periods of days before stable reproducible signals are achieved. The present devices show steady signals on the initial heatup.

The configuration disclosed in this invention can be used in all types of mixed-potential sensors that utilize a solid-electrolyte and metal or alloy electrodes. A specific application is a home CO sensor for room air monitoring. The Pt-wire/I $Ce_{0.8}Gd_{0.2}O_{1.9}$/Au-wire sensor has been tested for the measurement of CO in room air. This sensor with an activated carbon filter has been found to meet the sensitivity, response time, interference and stability standards stated in the UL 2034 (1995) standards. The sensor gives a 40 mV response for 100 ppm of CO with a response time <1 minute, and shows <2 mV interference for contaminants like methane, isopropanol, ethanol and heptane. The sensor has also been found to be stable for up to 2 months of continuous operation at 400° C.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A mixed potential electrochemical sensor for the detection of gases comprising:
    a ceria-based electrolyte having a surface for exposing to the gases to be detected;
    a reference wire electrode and a sensing wire electrode extending through the surface of the electrolyte and fixed within the electrolyte as the electrolyte is compressed and sintered.

2. The sensor according to claim 1 wherein the reference wire electrode is Pt.

3. The sensor according to claim 1, wherein the sensing wire electrode is Au or Rh.

4. The sensor according to claim 1, wherein the ceria-based electrolyte is $Ce_{1-x}A_xO_{2-x/2}$, where $0 \leq x \leq 0.25$ and A is selected from Y, Sc, or Lanthanide.

5. The sensor according to claim 4, wherein the reference wire electrode is Pt.

6. The sensor according to claim 4, wherein the sensing wire electrode is selected from the group consisting of Au, Ag, Pd, and Rh.

* * * * *